US005783174A

United States Patent [19]
Deckner

[11] Patent Number: 5,783,174
[45] Date of Patent: Jul. 21, 1998

[54] PHOTOSTABLE SUNSCREEN COMPOSITIONS

[75] Inventor: George Endel Deckner, Cincinnati, Ohio

[73] Assignee: The Procter & Gamble Company, Cincinnati, Ohio

[21] Appl. No.: 979,144

[22] Filed: Nov. 26, 1997

Related U.S. Application Data

[63] Continuation of Ser. No. 632,696, Apr. 16, 1996, abandoned, which is a continuation of Ser. No. 428,788, Apr. 24, 1995, which is a continuation of Ser. No. 227,912, Apr. 15, 1994, which is a continuation of Ser. No. 54,465, Apr. 28, 1993, which is a continuation of Ser. No. 929,612, Aug. 13, 1992.

[51] Int. Cl.$^6$ ............................. A61K 7/42; A61K 7/00
[52] U.S. Cl. ..................... 424/59; 424/60; 424/400; 424/401
[58] Field of Search ........................ 424/59, 60, 400, 424/401

[56] References Cited

U.S. PATENT DOCUMENTS

| 3,781,417 | 12/1973 | Welters et al. | 424/59 |
|---|---|---|---|
| 4,061,730 | 12/1977 | Kalopisses et al. | 424/59 |
| 4,387,089 | 6/1983 | DePolo | 424/59 |
| 4,489,057 | 12/1984 | Welters et al. | 424/47 |
| 4,671,956 | 6/1987 | Bouillon et al. | 424/59 |
| 4,804,531 | 2/1989 | Grollier | 424/47 |
| 4,820,508 | 4/1989 | Wortzman | 424/59 |
| 4,925,653 | 5/1990 | Grollier et al. | 424/47 |
| 5,028,417 | 7/1991 | Bhat et al. | 424/63 |
| 5,093,099 | 3/1992 | Haishi et al. | 424/63 |

FOREIGN PATENT DOCUMENTS

| 89/40158 | 3/1990 | Australia | A61K 7/42 |
|---|---|---|---|
| 0095109 | 8/1981 | Japan | 424/59 |
| 0081896 | 6/1983 | Japan | 514/944 |
| 2198944 | 6/1988 | United Kingdom | A61K 7/42 |
| WO 90/11067 | 10/1990 | WIPO | A61K 7/42 |

OTHER PUBLICATIONS

11R. Roelandts, "Which components in broad-spectrum sunscreens are most necessary for adequate UVA protection?", J. of the American Academy of Dermatology. vol. 25, No. 6, part 1, Dec. 1991, pp. 999–1004, 25(6)(1), Dec. 1991, pp. 999–1004.

12H. Gozenbach et al., "UVA Sunscreen In Vivo Effectiveness Measurements," Cosmetics & Toiletries, vol. 106, pp. 79–84, Nov. 91.

13M. C.G. van Praag et al., "Effect of Topical Sunscreens on the UV-Radiation Induced Suppression of the Alloactivating Capacity in Humin Skin In Vivo", J. of Invest. Derm. 97(4), pp. 629–633, Oct. 1991.

14A. M. Mommaas et al., Analysis of the Protective Effect of Topical Sunscreens . . . J. of Invest. Derm., 95(13), pp. 313–316, Sep. 1990.

15M. Garmyn et al., "Modification of Sunburn Cell Production . . . ", J. of Invest. Derm., 92(4), pp. 642–645, Apr. 1989.

16 Cosmetics & Toiletries, vol. 102, pp. 126, Mar. 1987.

17E. Azizi, "Efficacy of Topical Sunscreen Preparations . . . ", Israel J. of Med. Sci., 20(7), pp. 569–577, Jul. 1984.

18D. Moyal et al., Poster B22, "Colorimetric Assessment of Skin Immediate Pigment Darkening", 16th IFSCC Congress, Oct. 8–10, 1990.

19 Merck Tech Bulletin, "Eusolex® UV Filters for Cosmetics", pp. 65–67, 78–80, and 87–88.

*Primary Examiner*—Shelley A. Dodson
*Attorney, Agent, or Firm*—Leonard W. Lewis; Loretta J. Henderson

[57] ABSTRACT

The present invention relates to sunscreen compositions having improved photostability, especially in the UVA region, along with providing broad coverage in both the UVA and UVB regions. These compositions are achieved by combining a UVA-absorbing dibenzoylmethane sunscreen with a UVB-absorbing benzylidene camphor sunscreen. In highly preferred embodiments, these compositions also contain from about 0.1% to about 25% of an inorganic physical sunblock. These compositions are useful for protecting the skin from the harmful effects of ultraviolet radiation and for moisturizing the skin.

20 Claims, No Drawings

5,783,174

1

PHOTOSTABLE SUNSCREEN COMPOSITIONS

This is a continuation of application Ser. No.08/632,696, filed on Apr. 16, 1996, now abandoned which is a continuation of application Ser. No. 08/428,788, filed on Apr. 24, 1995, which is a continuation of Ser. No. 08/227,912 filed Apr. 15, 1994, which is a continuation of Ser. No. 08/054,465 filed Apr. 28, 1993, which is a continuation of Ser. No. 07/929,612 filed Aug. 13, 1992.

TECHNICAL FIELD

The present invention relates to sunscreen compositions having improved photostability, especially in the UVA region, along with providing broad coverage in both the UVA and UVB regions. These compositions are achieved by combining a UVA-absorbing dibenzoylmethane sunscreen with a UVB-absorbing benzylidene camphor sunscreen. In highly preferred embodiments, these compositions also contain from about 0.1% to about 25% of an inorganic physical sunblock. These compositions are useful for protecting the skin from the harmful effects of ultraviolet radiation.

BACKGROUND OF THE INVENTION

The damaging effects of sunlight on skin are well documented. The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema, but much more energy is required.

In addition to the short term hazard of erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs*, 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiation", *International Journal of Cosmetic Science*, 4, pp. 15–24 (1982); and U.S. Pat. No. 4,387,089, to DePolo, issued Jun. 7, 1983; which are all incorporated by reference herein.

Both sunscreen agents and physical sunblocks are commercially available to protect the skin from UV radiation. Without being limited by theory, it is believed that sunscreen agents exert their effects through chemical means, i.e., they absorb ultraviolet radiation so that it cannot penetrate the skin. Physical sunblocks scatter, reflect, and absorb ultraviolet radiation. See, Sayre, R. M. et al., "Physical Sunscreens", *J. Soc. Cosmet. Chem.*, vol. 41, no. 2, pp. 103–109 (1990).

Most commercially-available sunscreen agents are primarily UVB absorbers. The number of UVA absorbers is more

2 limited, with benzophenones and dibenzoylmethanes being the most well-known. U.S. Pat. No. 4,489,057, to Welters et al., issued Dec. 18, 1984, and U.S. Pat. No. 4,387,089, to DePolo, issued Jun. 7, 1983 both disclose dibenzoylmethane sunscreen agents. However, despite their highly desirable UVA absorption, dibenzoylmethane sunscreen agents tend to photodegrade during UV exposure, thereby reducing their effectiveness.

Previous researchers have attempted to overcome this photostability problem of dibenzoylmethanes. For example, British Patent GB 2,198,944, to Dellandre et al., published Jun. 29, 1988, teaches photostable sunscreen compositions having at least a 3:1 ratio of the sunscreen 3-(4-methylbenzylidene)camphor to 4,4'-methoxy-t-butyl-dibenzolymethane. However, this combination has the disadvantage of requiring more of the camphor derivative relative to the dibenzoylmethane than may be needed or desired, thus resulting in an imbalance of UVA to UVB protection and in formulation constraints.

In the present invention, it has been found that dibenzoylmethane containing compositions having improved photostability can be prepared by utilizing about a 1:1 ratio of a dibenzoylmethane sunscreen to a benzylidene camphor sunscreen. In highly preferred embodiments, these compositions also contain an inorganic physical sunblock, which in even further embodiments can be surface treated.

It is therefore an object of the present invention to provide sunscreen compositions having improved photostability, especially in the UVA region.

It is another object of the present invention to provide photostable sunscreen compositions which will prevent both acute effects (e.g., erythema) and chronic effects (e.g. photoaging and skin cancer) of exposure to sunlight and other sources of UV radiation.

It is a further object of the present invention to provide photostable sunscreen compositions which are not readily absorbed by the skin; which have a decreased chance for allergy, irritation, or toxicity problems resulting from daily or almost daily use; which are less susceptible to rub off; and which are cosmetically acceptable.

It is an even further object of the present invention to provide photostable sunscreen compositions which are suitable for daily use and which also moisturize the skin.

These and other objects will become readily apparent from the detailed description which follows.

SUMMARY OF THE INVENTION

The present invention relates to a sunscreen composition having improved photostability and broad UVA and UVB coverage, comprising:

(a) from about 0.1% to about 10% of a sunscreen compound (I) having the general structure

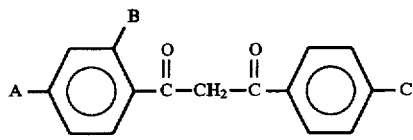

wherein A is a substituent selected from the group consisting of H, —OR, and —NR$_2$ wherein each R is independently H, or straight or branched chain alkyl having from about 1 to about 20 carbon atoms; B is a substituent selected from the group consisting of H and —OH; and C is a substituent selected from the group consisting of H, or straight or branched chain alkyl having from about 1 to about 20 carbon atoms;

(b) from about 0.1% to about 10% of a sunscreen compound (II) having the general structure

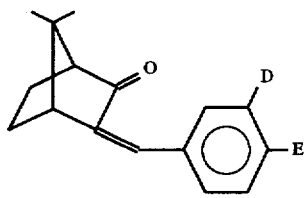

wherein D and E are substituents independently selected from the group consisting of H, straight or branched chain alkyl having from about 1 to about 20 carbon atoms, and —OR, wherein R is H or straight or branched chain alkyl having from about 1 to about 20 carbon atoms; and (c) a pharmaceutically-acceptable carrier;

wherein the weight ratio of sunscreen compound (I) to sunscreen compound (II) is from about 1:1.5 to about 1.5:1.

In further embodiments the present invention relates to a sunscreen composition having improved photostability and broad UVA and UVB coverage, comprising:

(a) from about 0.1% to about 10% of a sunscreen compound (I) having the general structure

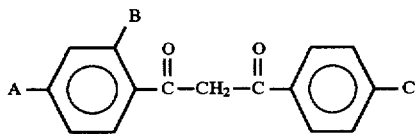

wherein A is a substituent selected from the group consisting of H, —OR, and —NR$_2$ wherein each R is independently H, or straight or branched chain alkyl having from about 1 to about 20 carbon atoms; B is a substituent selected from the group consisting of H and —OH; and C is a substituent selected from the group consisting of H, or straight or branched chain alkyl having from about 1 to about 20 carbon atoms;

(b) from about 0.1% to about 10% of a sunscreen compound (II) having the general structure

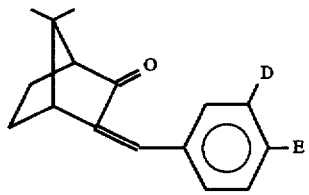

wherein D and E are substituents independently selected from the group consisting of H, straight or branched chain alkyl having from about 1 to about 20 carbon atoms, and —OR, wherein R is H, or straight or branched chain alkyl having from about 1 to about 20 carbon atoms;

(c) from about 0.1% to about 25% of a physical sunblock; and (d) a pharmaceutically-acceptable carrier;

wherein the weight ratio of sunscreen compound (I) to sunscreen compound (II) is from about 1:1.5 to about 1.5:1.

The present invention also relates to methods for protecting the skin of humans or lower animals from the effects of UVA and UVB wavelength radiation.

All percentages and ratios used herein are by weight of the total composition and all measurements made at 25° C., unless otherwise designated.

DETAILED DESCRIPTION OF THE INVENTION

The compositions of the instant invention comprise the following essential as well as optional components.

Dibenzoylmethane Sunscreen Compound

A UVA-absorbing dibenzoylmethane sunscreen compound is an essential component of the present invention. This sunscreen compound has the general structure

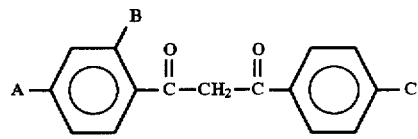

wherein A is a substituent selected from the group consisting of H, —OR, and —NR$_2$ wherein each R is independently H, or straight or branched chain alkyl having from about 1 to about 20 carbon atoms; B is a substituent selected from the group consisting of H and —OH; and C is a substituent selected from the group consisting of H, or straight or branched chain alkyl having from about 1 to about 20 carbon atoms.

Even though the dibenzoylmethane chromophore is represented as a 1,3-diketone it should be understood that this representation in no way excludes other tautomeric forms of the functional group such as the enol form. Thus whenever the 1,3-diketone form is designated, it is understood that all appropriate enol tautomers are also contemplated and included herein. These tautomeric enol forms of the dibenzoylmethane chromophore can be represented by the following tautomeric structures.

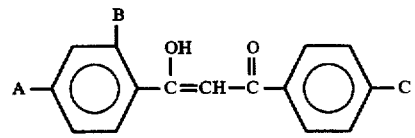

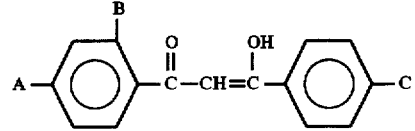

Dibenzoylmethane susncreen agents are described in U.S. Pat. No. 4,489,057, to Welters et al., issued Dec. 18, 1984, and U.S. Pat. No. 4,387,089, to DePolo, issued Jun. 7, 1983, both of which are incorporated by reference herein. See also, *Sunscreens: Development, Evaluation, and Regulatory Aspects*, edited by N. J. Lowe and N. A. Shaath, Marcel Dekker, Inc. (1990), which is incorporated by reference herein in its entirety. Examples of dibenzoylmethane susncreens useful herein include those selected from the group consisting of 4,4'-methoxy-t-butyldibenzoylmethane, 4-isopropyldibenzoylmethane, 4-methoxydibenzoylmethane, 2,4'-hydroxy-t-butyldibenzoylmethane, 2,4,4'-hydroxymethoxy-t- butyldibenzoylmethane, and mixtures thereof. More preferred are 4,4'-methoxy-t-butyldibenzoylmethane, 4-isopropyldibenzoylmethane, and mixtures thereof.

The sunscreen 4,4'-methoxy-t-butyldibenzoylmethane, which is also known as butyl methoxydibenzoylmethane, is commercially available under the trademark Parsol® 1789 from Givaudan. See CTFA International Cosmetic Ingredient Dictionary, fourth edition, 1991, pp. 68–69, which is incorporated by reference herein. The sunscreen 4-isopropyldibenzoylmethane, which is also known as isopropyl dibenzoylmethane, is commercially available under the trademark Eusolex® 8020 from Merck. See CTFA International Cosmetic Ingredient Dictionary, fourth edition, 1991, p. 267, which is incorporated by reference herein.

The dibenzoylmethane sunscreen compound of the instant invention is present from about 0.1% to about 10%, preferably from about 1% to about 5%, and most preferably from about 1.5% to about 2.5%.

Benzylidene Camphor Sunscreen Compound

A UVB-absorbing benzylidene camphor sunscreen compound is an essential component of the present invention. This sunscreen compound has the general structure

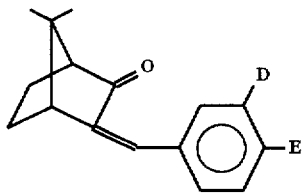

wherein D and E are substituents independently selected from the group consisting of H, straight or branched chain alkyl having from about 1 to about 20 carbon atoms, and —OR, where R is H, or straight or branched chain alkyl having from about 1 to about 20 carbon atoms. The camphor moiety of these susncreens can be derived from either D-camphor, L-camphor, or racemic D,L-camphor. U.S. Pat. No. 3,781,417, to Welters et al., issued Dec. 25, 1973, which is incorporated by reference herein, describes benzylidene camphor sunscreen compounds. See also, Sunscreens: Development, Evaluation, and Regulatory Aspects, edited by N. J. Lowe and N. A. Shaath, Marcel Dekker, Inc. (1990), which is incorporated by reference herein in its entirety. Examples of benzylidene camphor susncreens useful herein include those selected from the group consisting of 3-(4-methylbenzylidene) camphor, 3-benzylidene camphor, 3-(4-methoxybenzylidene) camphor, and mixtures thereof. More preferred are 3-(4-methylbenzylidene) camphor, 3-benzylidene camphor, and mixtures thereof. Most preferred is 3-(4-methylbenzylidene) camphor.

The sunscreen 3-(4-methylbenzylidene) camphor, which is also known as 4-methylbenzylidene camphor, is commercially available under the trademark Eusolex® 6300 from Merck and also from Rona. See CTFA International Cosmetic Ingredient Dictionary, fourth edition, 1991, pp. 317–318, which is incorporated by reference herein.

The benzylidene camphor sunscreen compound of the instant invention is present from about 0.1% to about 10%, preferably from about 1% to about 5%, and most preferably from about 1.5% to about 2.5%.

Ratio of Sunscreens

The weight ratio of UVA-absorbing dibenzoyl methane sunscreen to UVB-absorbing benzylidene camphor sunscreen is an important criticality of the present invention. The weight ratio of dibenzoyl methane sunscreen to benzylidene camphor sunscreen is from about 1:1.5 to about 1.5:1, preferably from about 1:1.25 to about 1.25:1, more preferably from about 1:1.1 to about 1.1:1, and most preferably about 1:1.

Physical Sunblocks

In highly preferred embodiments of the present invention, the compositions comprise an inorganic physical sunblock. Without being limited by theory, it is believed that the physical sunblock helps to provide more uniform coverage across the UVA and UVB regions.

Inorganic physical sunblocks useful herein include those selected from the group consisting of titanium dioxide, iron oxides, zinc oxide, silica, mica, and mixtures thereof. More preferred are those selected from the group consisting of titanium dioxide, iron oxides, and zinc oxide. Most preferred is titanium dioxide.

Titanium dioxide, iron oxides, zinc oxide, silica, and mica are described in CTFA International Cosmetic Ingredient Dictionary, Fourth Edition (1991), pp. 257–259, 324–326, 528–529, 611–612, and 649, which are incorporated by reference herein.

When titanium dioxide is selected as a physical sunblock for use herein, the titanium dioxide can have an anatase, rutile, or amorphous structure. The titanium dioxide preferably has a mean particle size from about 1 nm to about 100 nm, more preferably from about 15 nm to about 50 nm, and most preferably from about 30 nm to about 50 nm. The titanium dioxide particles can be uncoated or can be coated with a variety of materials including, but not limited to, amino acids; aluminum compounds such as alumina, aluminum stearate, aluminum laurate and the like; carboxylic acids and their salts, e.g., stearic acid and its salts; phospholipids such as lecithin; organic silicone compounds; inorganic silicon compounds such as silica, silicates; and mixtures thereof. Various grades and forms of titanium dioxide are described in CTFA International Cosmetic Ingredient Dictionary, Fourth Edition (1991), pp. 318–319; U.S. Pat. No. 4,820,508 to Wortzman, issued Apr. 11, 1989; and World Patent No. WO 90/11067 to Elsom et al., published Oct. 4, 1990; these three references are incorporated by reference herein in their entirety. See also, Sunscreens: Development, Evaluation, and Regulatory Aspects, edited by N. J. Lowe and N. A. Shaath, Marcel Dekker, Inc. (1990), which is incorporated by reference herein in its entirety.

Suitable grades of titanium dioxide for use in the compositions of the present invention are available commercially such as the MT micronized series distributed by Tri-K Industries (Emerson, N.J.), and manufactured by Tayca (Japan). These micronized titanium dioxides generally have a mean primary particle size ranging from about 10 nm to about 50 nm. For example, titanium dioxide having a mean primary particle size of about 15 nm is available under the trade designations MT-150W (uncoated) and MT-100T (coated with stearic acid and aluminum compounds). Uncoated titanium dioxides having mean primary particle sizes of around 35 nm and around 50 nm are available under the trade designations MT-500B and MT-600B, respectively. A titanium dioxide having a mean primary particle size of around 35 nm and coated with stearic acid, alumina, and silica is available under the trade name designation MT-500SA. Other coated titanium dioxides include MT-100F (modified with stearic acid and iron hydroxide and having a mean primary particle size around 15 nm), and MT-100S (treated with lauric acid and aluminum hydroxide and having a mean primary particle size around 15 nm). Mixtures of two or more types and particle size variations of titanium dioxide can be used in the present invention.

The titanium dioxide is present from about 0.1% to about 25% of the weight of the total composition, more preferably from about 0.5% to about 5%, and most preferably from about 1% to about 4%.

Pharmaceutically-Acceptable Carrier

The compositions of the instant invention comprise as a necessary component a safe and effective amount of a pharmaceutically-acceptable carrier which can be of a variety of different forms. By "pharmaceutically-acceptable" is meant that the carrier comprises common pharmaceutical and cosmetic ingredients which are typically used in the industry and which are generally recognized as safe for human contact. The topical carrier can be in the form of an emulsion including, but not limited to, oil-in-water, water-in-oil, water-in-oil-in-water, and oil-in-water-in-silicone emulsions. These emulsions can cover a broad range of consistencies including thin lotions (which can also be suitable for spray or aerosol delivery), creamy lotions, light creams, heavy creams, and the like. Other suitable topical carriers include anhydrous liquid solvents such as oils and alcohols; aqueous-based single phase liquid solvents (e.g. hydro-alcoholic solvent systems); anhydrous solids and semisolids (such as gels and sticks); and aqueous based gel and mousse systems. Examples of topical carrier systems useful in the present invention are described in the following four references all of which are incorporated herein by reference in their entirety: "Sun Products Formulary" Cosmetics & Toiletries, vol. 105, pp. 122–139 (December 1990); "Sun Products Formulary", Cosmetics & Toiletries, vol. 102, pp. 117–136 (March 1987); U.S. Pat. No. 4,960,764 to Figueroa et al., issued Oct. 2, 1990; and U.S. Pat. No. 4,254,105 to Fukuda et al., issued Mar. 3, 1981.

The pharmaceutically-acceptable topical carriers, in total, typically comprise from about 0.1% to about 99.8% by weight of the sunscreen compositions of the present invention, preferably from about 80% to about 99%, and most preferably from about 85% to about 95%.

A preferred topical carrier of the compositions of the instant invention is an oil-in-water type emulsion.

Optional Components

Emulsifiers

An optional component of the compositions of the instant invention is an emulsifier. Suitable emulsifiers can include any of a wide variety of nonionic, cationic, anionic, and zwitterionic emulsifiers disclosed in the prior patents and other references. See McCutcheon's, Detergents and Emulsifiers, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973; these four references are incorporated herein by reference in their entirety.

Suitable emulsifier types include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps and mixtures thereof.

Suitable emulsifiers can include, but are not limited to, polyethylene glycol 20 sorbitan monolaurate (Polysorbate 20), polyethylene glycol 5 soya sterol, Steareth-20, Ceteareth-20, PPG-20 methyl glucose ether distearate, Ceteth-10, Polysorbate 80, cetyl phosphate, potassium dicetyl/cetyl phosphate, diethanolamine dicetyl/cetyl phosphate, triethanolamine dicetyl/cetyl phosphate, tromethamine dicetyl/cetyl phosphate, Polysorbate 60, glyceryl stearate, PEG-100 stearate, and mixtures thereof.

The emulsifiers can be used individually or as a mixture of two or more and comprise from about 0.1% to about 10%, preferably from about 1% to about 7%, and most preferably from about 1% to about 5% of the compositions of the present invention.

Humectants/Moisturizers/Skin Conditioners

A highly preferred optional component of the compositions of the instant invention is at least one humectant/moisturizer/skin conditioner. A variety of these materials can be employed and each can be present at a level of from about 0.1% to about 20%, more preferably from about 0.5% to about 10% and most preferably from about 1% to about 5%. These materials include urea; guanidine; glycolic acid and glycolate salts (e.g. ammonium and quaternary alkyl ammonium); lactic acid and lactate salts (e.g. ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; polyethylene glycol; sugars and starches; sugar and starch derivatives (e.g., alkoxylated glucose); hyaluronic acid; lactamide monoethanolamine; acetamide monoethanolamine; and mixtures thereof.

Preferred humectants/moisturizers/skin conditioners useful in the compositions of the methods of the present invention are the $C_3$–$C_6$ diols and triols, and also aloe vera gel. Especially preferred is the triol, glycerol, and also aloe vera gel.

Carboxylic Acid Copolymers

Another optional component of the compositions of the instant invention is a carboxylic copolymer (acrylic acid copolymer). These materials are known as carbomers and are available under the Carbopol® trademark from B. F. Goodrich). Also useful are the acrylate/alkyl acrylate crosspolymers such as Acrylates/C10–C30 Alkyl Acrylate Crosspolymer (available as Pemulen TR-1, Pemulen TR-2, and Carbopol 1342 from B. F. Goodrich). These polymers are more fully described in U.S. Pat. No. 4,509,949, to Huang et al., issued Apr. 5, 1985; U.S. Pat. No. 2,798,053, to Brown, issued Jul. 2, 1957; and CTFA International Cosmetic Ingredient Dictionary, fourth edition, 1991, pp. 12 and 80; these references are all incorporated herein by reference in their entirety.

These polymers comprise from about 0.025% to about 0.75%, preferably from about 0.05% to about 0.50% and most preferably from about 0.10% to about 0.50% of the compositions useful herein.

Emollients

The compositions of the present invention can also optionally comprise at least one emollient. Examples of suitable emollients include, but are not limited to, volatile and non-volatile silicone oils (e.g., dimethicone, cyclomethicone, dimethiconol, and the like), highly branched hydrocarbons, and non-polar carboxylic acid and alcohol esters, and mixtures thereof. Emollients useful in the instant invention are further described in U.S. Pat. No.

4,919,934, to Deckner et al., issued Apr. 24 1990, which is incorporated herein by reference in its entirety.

The emollients can typically comprise in total from about 0.5% to about 50%, preferably from about 0.5% to about 25%, and more preferably from about 0.5% to about 10% by weight of the compositions useful in the present invention.

Optional Components

A variety of additional ingredients can be incorporated into the compositions useful in the present invention.

The compositions can optionally comprise additional sunscreens. When used, additional sunscreens can comprise from about 0.1% to about 20% of the compositions useful herein. Exact amounts will vary depending upon the sunscreen chosen and the desired Sun Protection Factor (SPF). SPF is a commonly used measure of photoprotection of a sunscreen against erythema. See Federal Register, Vol. 43, No. 166, pp. 38206–38269, Aug. 25, 1978, which is incorporated herein by reference in its entirety.

Non-limiting examples of other additional ingredients include other vitamins and derivatives thereof (e.g., ascorbic acid, Vitamin E, tocopheryl acetate, retinoic acid, retinal, retinoids, and the like); thickening agents (e.g. polyacrylamide and $C_{13-14}$ isoparaffin and laureth-7, available as Sepigel from Seppic Corporation); resins; gums; cationic polymers and thickeners (e.g., cationic guar gum derivatives such as guar hydroxypropyltrimonium chloride and hydroxypropyl guar hydroxypropyltrimonium chloride, available as the Jaguar C series from Rhone-Poulenc; copolymers of acrylamide and a cationic acrylate (available as Salcare SC92 from Allied Colloid); polymers for aiding the film-forming properties and substantivity of the composition (such as a copolymer of eicosene and vinyl pyrrolidone, an example of which is available from GAF Chemical Corporation as Ganex V-220®); preservatives for maintaining the antimicrobial integrity of the compositions; skin penetration aids such as DMSO, 1-dodecyl-azacycloheptan-2-one (available as Azone from the Upjohn Co.) and the like; anti-acne medicaments (resorcinol, salicylic acid, erythromycin, benzoyl peroxide, and the like); artificial tanning agents such as dihydroxyacetone and the like; skin bleaching (or lightening) agents including but not limited to hydroquinone, ascorbic acid, kojic acid and sodium metabisulfite; antioxidants; chelators and sequestrants; and aesthetic components such as fragrances, pigments, colorings, essential oils, skin sensates, astringents, skin soothing agents, skin healing agents and the like, nonlimiting examples of these aesthetic components include clove oil, menthol, camphor, eucalyptus oil, eugenol, menthyl lactate, witch hazel distillate, allantoin, bisabalol, dipotassium glycyrrhizinate and the like.

Methods for Protecting and Moisturizing the Skin

The compositions of the present invention are useful for the protection of the skin from the harmful effects of UVA and UVB radiation. These compositions can also be used to help mositurize the skin. Typically, these compositions are applied to the skin in an effective amount, which is about 2 mg/cm$^2$. These compositions can be used on a regular or daily basis.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

EXAMPLES I–V

Daily Moisturizing Lotions Containing Sunscreens

The following ingredients are combined to form an oil-in-water emulsion using conventional mixing techniques.

| Ingredients | % Weight | | | | |
| --- | --- | --- | --- | --- | --- |
| | I | II | III | IV | V |
| Water | QS100 | QS100 | QS100 | QS100 | QS100 |
| Acrylates/C10–30 Alkyl Acrylate Crosspolymer | 0.125 | 0.125 | 0.125 | 0.125 | 0.125 |
| Disodium EDTA | 0.05 | 0.05 | 0.05 | 0.05 | 0.05 |
| Carbomer 954 | 0.20 | 0.20 | 0.20 | 0.20 | 0.20 |
| Glycerin | 1.00 | 1.00 | 1.00 | 1.00 | 1.00 |
| Hexylene Glycol | 2.00 | 2.00 | 2.00 | 2.00 | 2.00 |
| Methylparaben | 0.25 | 0.25 | 0.25 | 0.25 | 0.25 |
| Dimethicone (and) Cyclomethicone[1] | 0.75 | 0.75 | 0.75 | 0.75 | 0.75 |
| PEG-10 Soya Sterol | 0.10 | 0.10 | 0.10 | 0.10 | 0.10 |
| Stearic Acid | 1.00 | 1.00 | 1.00 | 1.00 | 1.00 |
| Cetyl Alcohol | 1.00 | 1.00 | 1.00 | 1.00 | 1.00 |
| Cetyl Palmitate | 0.50 | 0.50 | 0.50 | 0.50 | 0.50 |
| DEA Cetyl Phosphate | 0.75 | 0.75 | 0.75 | 0.75 | 0.75 |
| Castor Oil | 0.05 | 0.05 | 0.05 | 0.05 | 0.05 |
| Aluminum Starch Octenylsuccinate | 0.50 | 0.50 | 0.50 | 0.50 | 0.50 |
| Ethylparaben | 0.15 | 0.15 | 0.15 | 0.15 | 0.15 |
| Butyl Methoxydibenzoylmethane | 1.50 | 1.50 | 2.00 | 1.90 | 1.45 |
| 4-Methylbenzylidene Camphor | 1.50 | 1.50 | 2.00 | 2.00 | 1.50 |
| C12–15 Alkyl Benzoate | 10.0 | 10.0 | 10.0 | 10.0 | 10.0 |
| PVP/Eicosene Copolymer | 0.50 | 0.50 | 0.50 | 0.50 | 0.50 |
| Titanium Dioxide[2] | 1.50 | 1.50 | 2.00 | — | — |
| Titanium Dioxide Coated[3] | — | — | — | 1.50 | 1.50 |
| Zinc Oxide[4] | 0.80 | — | — | — | 0.25 |
| Iron Oxide | — | — | — | — | 0.25 |
| Triethanolamine (99%) | 0.73 | 0.73 | 0.73 | 0.73 | 0.73 |
| Benzyl Alcohol | 0.30 | 0.30 | 0.30 | 0.30 | 0.30 |

[1] Available as Dow Corning 200/350 Fluid.
[2] Available as MT-500B and/or MT-600B from Tri-K Industries Inc., Emerson, N.J.
[3] Available as MT-500SA (coated wtih stearic acid, alumina, and silica) from Tri-K Industries.
[4] Available as a suspension in octyl palmitate from Tioxide Corp.

The resulting emulsion is useful for topical application to the skin as a daily moisturizer and to provide protection from the harmful effects of ultraviolet radiation.

EXAMPLE VI

Sunscreen Oil

A sunscreen oil is prepared by combining the following components utilizing conventional mixing techniques.

| Ingredients | % Weight |
| --- | --- |
| Mineral Oil | QS100 |
| Butyl Methoxydibenzoylmethane | 3.00 |
| 4-Methylbenzylidene Camphor | 3.00 |
| $C_{12-15}$ Alcohols Benzoate | 15.00 |
| Isopropyl Myristate | 2.00 |
| Sorbitan Oleate | 1.50 |
| Propylparaben | 0.50 |
| D&C Red #17 | 0.002 |

The above ingredients are combined and heated until the propylparaben is dissolved.

This sunscreen oil is useful for topical application to the skin to provide protection from the harmful effects of ultraviolet radiation.

EXAMPLE VII

Anhydrous Sunscreen Gel

An anhydrous sunscreen gel is prepared by combining the following components utilizing conventional mixing techniques.

| Ingredients | % Weight |
| --- | --- |
| Mineral Oil | QS100 |
| Butyl Methoxydibenzoylmethane | 2.45 |
| 4-Methylbenzylidene Camphor | 2.50 |
| Titanium Dioxide | 0.50 |
| Petrolatum | 15.00 |
| Paraffin Wax | 10.00 |
| Ozokerite | 8.00 |
| Isopropyl Myristate | 5.00 |
| Fragrance | 0.50 |
| D&C Yellow #10 Aluminum Lake and Mineral Oil and Petrolatum[1] | 0.545 |
| D&C Red #17 | 0.0055 |
| Propylparaben | 0.100 |
| $C_{12-15}$ Alcohols Benzoate | 10.00 |
| Butylparaben | 0.03 |

[1]Available as Opatint Yellow OD-2169 from Colorcon.

The above ingredients are combined and heated with mixing until dispersed.

This anhydrous sunscreen gel is useful for topical application to the skin to provide protection from the harmful effects of ultraviolet radiation.

EXAMPLE VIII

Hydroalcoholic Sunscreen Gel

A hydroalcoholic sunscreen gel is prepared by combining the following components utilizing conventional mixing techniques.

| Ingredients | % Weight |
| --- | --- |
| Phase A | |
| Water | QS100 |
| Hydroxyethyl cellulose | 0.90 |
| TEA-Coco-Hydrolyzed Animal Protein | 2.00 |
| Hydrolyzed Animal Collagen[1] | 1.00 |
| Butyl Methoxydibenzoylmethane | 1.50 |
| 4-Methylbenzylidene Camphor | 1.50 |
| Titanium Dioxide | 0.10 |
| Glycerin | 1.00 |
| Phase B | |
| Soluble Animal Collagen[2] | 3.00 |
| Phase C | |
| Alcohol SD-40 | 20.00 |
| Polysorbate 20 | 0.80 |
| Fragrance | 0.50 |

[1]Available as Polypro 5000 from Geo. A. Hormel & Co.
[2]Available as Sollagen from Geo. A. Hormel & Co.

Heat water to 60°–65° C. and sprinkle the hydroxyethyl cellulose into the stirred water. Allow to fully dissolve to a clear solution. Stop heating and add remaining Phase A ingredients. Cool to below 35° C. and add Phase B. Mix Phase C ingredients and add to the mixture of Phases A and B.

This hydroalcoholic gel is useful for topical application to the skin to provide protection from the harmful effects of ultraviolet radiation.

EXAMPLE IX

Lip Protecting Stick

A lip protecting stick is prepared by combining the following components utilizing conventional mixing techniques.

| Ingredients | % Weight |
| --- | --- |
| Mineral Oil | QS100 |
| Butyl Methoxydibenzoylmethane | 2.50 |
| 4-Methylbenzylidene Camphor | 2.50 |
| Titanium Dioxide | 1.00 |
| Petrolatum | 15.94 |
| $C_{12-15}$ Alcohols Benzoate | 13.00 |
| Ozokerite Wax | 13.00 |
| Candililla Wax | 13.00 |
| Oleyl Alcohol | 8.00 |
| Tocopheryl Acetate | 1.00 |
| Propylparaben | 0.10 |

The ingredients are combined together and heated with mixing until uniform, and the resulting mixture is poured into appropriate containers and allowed to harden.

This lip protecting stick is useful for topical application to the lips to provide protection from the harmful effects of ultraviolet radiation.

EXAMPLE X

Sunscreen Spray Emulsion Lotion

A sunscreen spray emulsion is prepared by combining the following components utilizing conventional mixing techniques.

| Ingredients | % Weight |
| --- | --- |
| Phase A | |
| Water | QS100 |
| Carbomer 1342 | 0.10 |
| Disodium EDTA | 0.10 |
| Phase B | |
| Butyl Methoxydibenzoylmethane | 2.40 |
| 4-Methylbenzylidene Camphor | 2.50 |
| Titanium Dioxide | 0.10 |
| PVP Eicosene Copolymer | 1.00 |
| Stearic Acid | 0.15 |
| Simethicone | 0.01 |
| Stearoxy Dimethicone | 0.50 |
| $C_{12-15}$ Alcohols Benzoate | 10.00 |
| Phase C | |
| Water | 2.00 |
| Triethanolamine (99%) | 0.175 |
| Phase D | |
| Water | 2.00 |
| Butylene Glycol | 2.00 |
| DMDM Hydantoin (and) Iodopropynyl Butylcarbamate | 0.25 |
| Dexpanthenol | 0.50 |
| Phase E | |
| Fragrance | 0.30 |
| Cyclomethicone | 2.00 |

This sunscreen spray emulsion is useful for topical application to the skin to provide protection from the harmful effects of ultraviolet radiation.

What is claimed is:

1. A sunscreen composition having improved photostability and broad UVA and UVB coverage, comprising:
   (a) from about 0.1% to about 10% of a sunscreen compound (I) having the general structure

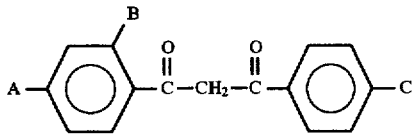

wherein A is a substituent selected from the group consisting of H, —OR, and —NR$_2$ wherein each R is independently H, or straight or branched chain alkyl having from about 1 to about 20 carbon atoms; B is a substituent selected from the group consisting of H and —OH; and C is a substituent selected from the group consisting of H, or straight or branched chain alkyl having from about 1 to about 20 carbon atoms;
   (b) from about 0.1% to about 10% of a sunscreen compound (II) having the general structure

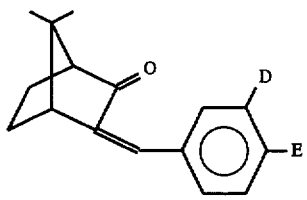

wherein D and E are substituents independently selected from the group consisting of H, straight or branched chain alkyl having from about 1 to about 20 carbon atoms, and —OR, wherein R is H, or straight or branched chain alkyl having from about 1 to about 20 carbon atoms;
   (c) from about 0.1% to about 25% of a physical sunblock; and
   (d) a pharmaceutically-acceptable carrier;
   wherein the weight ratio of sunscreen compound (I) to sunscreen compound (II) is from about 1:1.5 to about 1.5:1.

2. A sunscreen composition according to claim 1 comprising from about 0.5% to about 5% of sunscreen compound (I); from about 0.5% to about 5 of sunscreen compound (II); and from about 1% to about 4% of a physical sunblock.

3. A sunscreen composition according to claim 2 wherein the weight ratio of sunscreen compound (I) to sunscreen compound (II) is from about 1:1.1 to about 1.1:1.

4. A sunscreen composition according to claim 3 wherein the weight ratio of sunscreen compound (I) to sunscreen compound (II) is about 1:1.

5. A sunscreen composition according to claim 4 wherein sunscreen compound (I) is selected from the group consisting of 4,4'-methoxy-t-butyldibenzoylmethane, 4-isopropyldibenzoylmethane, 4-methoxydibenzoylmethane, 2,4'-hydroxy-t-butyldibenzoylmethane, 2,4,4'-hydroxy-methoxy-t-butyldibenzoylmethane, and mixtures thereof; sunscreen compound (II) is selected from the group consisting of 3-(4-methylbenzylidene) camphor, 3-benzylidene camphor, 3-(4-methoxybenzylidene) camphor, and mixtures thereof; and said physical sunblock is selected from the group consisting of titanium dioxide, iron oxides, zinc oxide, silica, mica, and mixtures thereof.

6. A sunscreen composition according to claim 5 wherein sunscreen compound (I) is selected from the group consisting of 4,4'-methoxy-t-butyldibenzoylmethane, 4-isopropyldibenzoylmethane, and mixtures thereof; sunscreen compound (II) is 3-(4-methylbenzylidene) camphor; and said physical sunblock is selected from the group consisting of titanium dioxide, iron oxides, zinc oxide, and mixtures thereof.

7. A sunscreen composition according to claim 6 wherein sunscreen compound (I) is 4,4'-methoxy-t-butyldibenzoylmethane, and said physical sunblock is titanium dioxide.

8. A sunscreen composition according to claim 6 wherein sunscreen compound (I) is 4-isopropyldibenzoylmethane, and said physical sunblock is titanium dioxide.

9. A sunscreen composition according to claim 1 wherein said physical sunblock has been surface treated.

10. A sunscreen composition according to claim 9 wherein said physical sunblock is selected from titanium dioxide which has been surface treated with a mixture of stearic acid, alumina, and silica.

11. A sunscreen composition according to claim 1 wherein said pharmaceutically-acceptable carrier is an oil-in-water emulsion.

12. A sunscreen composition according to claim 7 wherein said pharmaceutically-acceptable carrier is an oil-in-water emulsion.

13. A sunscreen composition according to claim 12 which further comprises glycerol, a silicone fluid, a carboxylic acid copolymer, and DEA-cetylphosphate.

14. A sunscreen composition according to claim 1 wherein said pharmaceutically-acceptable carrier is a water-in-oil emulsion.

15. A sunscreen composition according to claim 1 wherein said pharmaceutically-acceptable carrier is an oil.

16. A sunscreen composition according to claim 1 wherein said pharmaceutically-acceptable carrier is an aqueous-based lotion or gel.

17. A sunscreen composition according to claim 1 wherein said pharmaceutically-acceptable carrier is an anhydrous gel.

18. A method for protecting the skin of humans or lower animals from the effects of UVA and UVB wavelength radiation, said method comprising topically applying to the skin of the human or lower animal an effective coating of a sunscreen composition according to claim 1.

19. A method for protecting the skin of humans or lower animals from the effects of UVA and UVB wavelength radiation, said method comprising topically applying to the skin of the human or lower animal an effective coating of a sunscreen composition according to claim 13.

20. A sunscreen composition according to claim 9 wherein the sunscreen compound (I) is selected from the group consisting of 4,4'-methoxy-t-butyldibenzoylmethane, 4-isopropyldibenzoylmethane, and mixtures thereof.

* * * * *

UNITED STATES PATENT AND TRADEMARK OFFICE
CERTIFICATE OF CORRECTION

PATENT NO.    : 5,783,174

DATED         : July 21, 1998

INVENTOR(S)   : George Endel Deckner

It is certified that error appears in the above-identified patent and that said Letters Patent is hereby corrected as shown below:

At column 2, line 15 "dibenzolymethane" should read --dibenzoylmethane--.

At column 9, line 23 "retinal" should read --retinol--.

At column 13, line 48 "5of" should read --5% of--.

Signed and Sealed this

Tenth Day of November 1998

Attest:

BRUCE LEHMAN

Attesting Officer

Commissioner of Patents and Trademarks